(12) United States Patent
Starkey

(10) Patent No.: US 7,197,952 B2
(45) Date of Patent: Apr. 3, 2007

(54) TESTING METHOD FOR BALL MILLS

(75) Inventor: John H. Starkey, Oakville (CA)

(73) Assignee: Outokumpu Technology Oyj, Espoo (FI)

( * ) Notice: Subject to any disclaimer, the term of this patent is extended or adjusted under 35 U.S.C. 154(b) by 30 days.

(21) Appl. No.: 10/820,373

(22) Filed: Apr. 8, 2004

(65) Prior Publication Data

US 2005/0223798 A1    Oct. 13, 2005

(51) Int. Cl.
*G01N 33/00* (2006.01)

(52) U.S. Cl. .................................... 73/866

(58) Field of Classification Search ............. 73/866, 73/11.01, 863.91
See application file for complete search history.

(56) References Cited

U.S. PATENT DOCUMENTS

| | | | | |
|---|---|---|---|---|
| 3,791,218 A | * | 2/1974 | Pennington | 73/863.54 |
| 3,865,718 A | * | 2/1975 | Tveter et al. | 209/166 |
| 3,940,997 A | * | 3/1976 | Hudson | 73/866 |
| 5,211,920 A | * | 5/1993 | Polizzotti | 423/29 |
| 5,289,728 A | * | 3/1994 | Johanson et al. | 73/866 |
| 6,089,079 A | * | 7/2000 | Rosenblum et al. | 73/73 |
| 2003/0038198 A1 | | 2/2003 | Starkey | |

FOREIGN PATENT DOCUMENTS

GB    404608    1/1934

\* cited by examiner

*Primary Examiner*—Robert Raevis
(74) *Attorney, Agent, or Firm*—Morgan & Finnegan, LLP

(57) ABSTRACT

The invention relates to a testing method for designing a semiautogenous or an autogenous grinding circuit with at least one ball mill for grinding ore. In the method the ore is tested in two separate testing steps using the same testing sample of ore.

1 Claim, No Drawings

TESTING METHOD FOR BALL MILLS

This invention relates to a testing method for designing a semiautogenous or an autogenous grinding circuit with at least one ball mill.

The feed to autogenous and semiautogenous mills is an important variable in the performance of a grinding circuit. The feed can be essentially influenced by the grinding circuit and, in some cases, by the mining operations itself. Autogenous mills use the feed material as the grinding media. The larger the particle the more energy can be imparted, and therefore the more impact breakage likely. In semiautogenous milling, steel grinding media is added to the mill. The size of the grinding media has an essential impact on the rate of breakage, for instance with a ball of 125 mm equivalent in mass to a rock of approximately 180 mm. Therefore, the feed required for semiautogenous mills does not have to be as coarse as that for autogenous mills.

In order to determine the energy and thus power required for grinding in autogenous or semiautogenous mills there are developed different kinds of tests. One test is called Bond ball mill test, which results a parameter providing a standard net power requirement for grinding. The test is conducted on ore stage-crushed to minus 6 mesh, i.e. the ore is crushed so that all ore is going through a screen having quadratic apertures of 3.35 millimeter (6 mesh) and further ground to minus 100 mesh, going through a screen having quadratic apertures of 0.149 millimeter. The test requires 5 to 10 kg of minus 2.362 millimeter (8 mesh) ore. The Bond ball mill test enables basic grinding power requirement to be determined, from the feed 80% passing size to circuit 80% passing size. The Bond ball mill test is designed to predict power in wet ball mill grinding circuit operating at a 250% circulating load. However, moving away from this condition reduces the accuracy of the test. Further, the Bond ball mill test does not predict the behavior of large rocks in a grinding circuit where the mode of breakage is impact dominated. The test has been further developed to include other type of tests to provide information to make the projection for coarse grinding, namely autogenous or semiautogenous grinding. The other tests are for instance Bond Impact test and JK impact test. Characteristic to these tests are testing large number of single pieces of the tested material. The samples are prepared separately from the Bond ball mill test and thus the representativeness of the two samples is questioned as well as the sample size for testing will be increased.

It is also developed a test, the Starkey test, to predict semiautogenous mill specific power requirements using only minus 12.7 millimeter (0,5 mesh) material. The Starkey test uses a small 300 mm in diameter and 100 mm long laboratory scale mill with a small ball charge of 25 mm balls to grind the test sample of 2 kg. The objective is to establish the grinding time required to grind the ore to 80% passing 1.7 millimeter (10 mesh), the closing screen size. The Starkey test demonstrates a strong correlation between the grinding time for ores and their corresponding semiautogenous mill specific power draw. The Starkey test is an attractive alternative to tests requiring large sample size.

The object of the present invention is to eliminate some drawbacks of the prior art and to achieve an improved testing method for designing a semiautogenous or an autogenous grinding circuit with at least one ball mill. The essential features of the invention are enlisted in the appended claims.

In accordance with the invention, the testing method for designing a semiautogenous or an autogenous grinding circuit with at least one ball mill contains two separate testing steps using the same sample for determining the energy requirements for a semiautogenous mill using balls as grinding media. The testing steps are arranged so that the first step for the testing method is a semiautogenous test, which is followed by a ball mill test. Due to the fact the test is carried out in two steps, one can make accurate estimation for capacity and energy requirement for the two products in respective process steps, thus optimize the energy distribution between the comminution stages. The first testing step is conventionally optimized for testing product size or transfer size to a subsequent grinding step ranging between 0.500 and 3.500 millimeter measured as the 80% passing point. In the second test the grinding process is extended to finer size range to make an accurate projection for the typical final grinding circuit product ranging between 0.045 and 0.150 millimeter measured as the 80% passing point. In the first testing step the resultant time and the ore specific gravity are used to calculate the required grinding energy, and the second testing step is used to determine the required ball mill energy to reach the predetermined grind size.

The sample for the testing method of the invention is advantageously between 2 to 10 kg, preferably 6 to 9 kg by weight of the ore to be tested. The ore sample is precrushed to the particle size of minus 1.25 inches (32 mm) and/or 80% of the particles passing a screen having mesh of 0.75 inches (19 mm).

The first step of the testing method, the semiautogenous test is carried out in a conveniently selected ball mill having a diameter of 490 millimeter and a length of 163 millimeter. The ball mill is advantageously in a range of 1:0.33 to 1:2 in diameter length ratio. The diameter length ratio is dependent on the required application type of energy transfer required to carry out the comminution process. The ore sample is ground in batch mode at the presence of steel balls.

The steel ball size is selected so that 55% of the balls is equal or larger than 2 inches and 45% of the balls is equal or larger than 1,5 inches in diameter. The steel weight is 16 kg. The grinding is continued until the entire ore weight is reduced to 80% passing a screen of having quadratic apertures of 1.68 millimeter (12 mesh). The resultant grinding time, grinding media, the ore specific gravity and revolutions of the ball mill are used to calculate required grinding energy advantageously in units of kilowatts per ton of ore, i.e. kW/t.

The energy calculation (SAG Energy) is done using the following equation (1):

$$SAG \text{ Energy } (kWh/t) = C \times \text{Actual } Revs \times (\text{Bulk } SG/\text{Weight } (g)) \quad (1),$$

wherein C is a constant defined by the mill dimension and speed having a value 17.66 for the given test arrangement, Actual Revs is the amount of revolutions in the ball mill, Bulk SG is the specific weight of the sample to be treated and Weight is the mass of the sample to be treated.

In the second step of the testing method, the test is based on the Bond ball mill. The product from the first step is then used for determination of the required ball mill energy for the secondary grinding stage to reach the target grinding size. The empirical formula to calculate Bond Mill Work Index (BWi) is presented in the equation (2)

$$BWi = \frac{44{,}5}{U_1^{0,23} G_{bh}^{0,82} \left( \frac{10}{\sqrt{U_{80}}} - \frac{10}{\sqrt{F_{80}}} \right)}, \quad (2)$$

wherein $U_1$ is the passing size in micrometer of the test sieve, $G_{bh}$ is the ball mill grindability and $U_{80}$ and $F_{80}$ are passing values in a mount of 80% in the sieve analysis for the product ($U_{80}$) and feed($F_{80}$) in micrometer.

Based on the results of the first and second testing steps a circuit of ball mills were sized and designed so that the resulted grinding energy was divided in ball mills so that the dimensions of each mill are reasonable for effective grinding of the ore tested.

Using the testing method of the invention for the same sample through both the testing steps the required sample size for one type of ore is limited and the same sample allows more testing for the same amount of investment. Also the result of two tests gives more accurate information of the tested ore. Further, the same sample is advantageous because the sample preparation for the second testing step is eliminated and the true feeding conditions are passed to the Bond ball mill testing. In the method of the invention, the fines generation in the first testing step is taken into account as the product from the first test is used for the second test without artificially manipulating the sample and the size distribution. This improves the accuracy of the test and reduces sample preparation stages.

EXAMPLE

The ore having a density of 3.03 kg/cm$^3$ was ground in the ball mill for the semiautogenous test. The grinding time was 1880 revolutions for a sample of 8065 g. Using the equation 1 the required grinding energy was calculated for a value of 12.5 kW/t ore. The ground ore from the semiautogenous test was then used for the Bond ball mill test. Using the results of the test the equation 2 gives for the ball mill energy a value of 15.0 kW/t ore.

The invention claimed is:

1. A testing method for designing a semiautogenous or an autogenous grinding circuit having at least one ball mill for grinding ore, the method comprising:

measuring an amount of time for grinding a predetermined mass of ore to a first predetermined size, in a first, semiautogenous step;

calculating a required grinding energy based on the measured time for grinding in the first step, mass of ore, mill characteristics and a measured specific gravity;

grinding in a ball mill, in a second step, the ore from the first step to a second predetermined size; and calculating, using the Bond Mill Work Index, a required ball mill energy for the second step required to obtain a desired final grind size.

* * * * *